US012806043B2

(12) United States Patent
Farris et al.

(10) Patent No.: US 12,806,043 B2
(45) Date of Patent: Nov. 24, 2026

(54) CONTROL METHOD FOR A POWERED KNEE ANKLE FOOT ORTHOSIS

(71) Applicant: Ekso Bionics Holdings, Inc., San Rafael, CA (US)

(72) Inventors: Ryan J. Farris, Dillsburg, PA (US); Spencer A. Murray, Aurora, OH (US); Skyler A. Dalley, Shaker Heights, OH (US)

(73) Assignee: Ekso Bionics Holdings, Inc., San Rafael, CA (US)

( * ) Notice: Subject to any disclaimer, the term of this patent is extended or adjusted under 35 U.S.C. 154(b) by 522 days.

(21) Appl. No.: 18/549,985

(22) PCT Filed: Mar. 15, 2021

(86) PCT No.: PCT/US2021/022287
§ 371 (c)(1),
(2) Date: Sep. 11, 2023

(87) PCT Pub. No.: WO2022/197280
PCT Pub. Date: Sep. 22, 2022

(65) Prior Publication Data
US 2024/0148522 A1 May 9, 2024

(51) Int. Cl.
*A61F 5/01* (2006.01)
*A61F 2/64* (2006.01)
(Continued)

(52) U.S. Cl.
CPC .................. *A61F 2/70* (2013.01); *A61F 2/64* (2013.01); *A61F 2/76* (2013.01); *A61F 5/0102* (2013.01);
(Continued)

(58) Field of Classification Search
None
See application file for complete search history.

(56) References Cited

U.S. PATENT DOCUMENTS 5,704,945 A * 1/1998 Wagner ..................... A61F 2/64 623/44
7,485,152 B2 * 2/2009 Haynes ..................... A61F 2/64 623/24
(Continued)

FOREIGN PATENT DOCUMENTS

CA 2762265 A1 * 10/2001 .............. F16F 9/535

OTHER PUBLICATIONS

International Search Report and Written Opinion of the International Searching Authority for corresponding International Patent Application No. PCT/US2021/022287, mailed Dec. 6, 2021.

*Primary Examiner* — Ann Hu
(74) *Attorney, Agent, or Firm* — Renner, Otto, Boisselle & Sklar, LLP

(57) ABSTRACT

A powered KAFO device includes an electronic control system that provides an enhanced operation to better approximate a human gait cycle for enhanced mobility assistance. Multiple gait cycles of stance substate control and swing substate control are implemented to perform walking. During stance control, the control system measures an error between a desired and an actual knee joint component angle, and operates the actuator assembly of the powered mobility assistance device to control the knee joint component to stabilize the knee joint component. During swing control, the electronic control system measures an error between a desired and an actual knee swing trajectory, and operates the actuator assembly to control the knee joint component to adjust toward the desired swing knee trajectory. The gait cycle further may include a neutral substate that transitions from the stance substate to the swing substate, in which actuator assembly releases the knee joint component.

14 Claims, 11 Drawing Sheets

(51) Int. Cl.

| | |
|---|---|
| ***A61F 2/70*** | (2006.01) |
| ***A61F 2/76*** | (2006.01) |
| ***A61H 3/00*** | (2006.01) |
| ***B25J 9/00*** | (2006.01) |

(52) U.S. Cl.
CPC . *A61F 2002/701* (2013.01); *A61F 2002/7625* (2013.01); *A61F 2005/0158* (2013.01)

(56) References Cited

U.S. PATENT DOCUMENTS

| | | | | |
|---|---|---|---|---|
| 7,985,193 | B2 * | 7/2011 | Thorsteinsson | A61B 5/4585 602/32 |
| 8,435,309 | B2 * | 5/2013 | Gilbert | A61F 2/582 623/24 |
| 9,693,883 | B2 | 7/2017 | Herr et al. | |
| 10,390,973 | B2 | 8/2019 | Tong et al. | |
| 11,642,272 | B2 * | 5/2023 | Dalley | A61H 1/0262 601/5 |
| 11,826,302 | B2 * | 11/2023 | Farris | A61F 5/0102 |
| 12,071,990 | B2 * | 8/2024 | Farris | A61H 1/0255 |
| 2006/0249315 | A1 * | 11/2006 | Herr | A61F 2/6607 623/47 |
| 2010/0023133 | A1 * | 1/2010 | Fairbanks | A61F 2/64 623/24 |
| 2011/0098828 | A1 * | 4/2011 | Balboni | A61F 2/60 623/40 |
| 2014/0172120 | A1 | 6/2014 | Steele et al. | |
| 2016/0074180 | A1 * | 3/2016 | Lenzi | A61F 2/6607 623/24 |
| 2016/0151176 | A1 | 6/2016 | Unluhisarcikli et al. | |
| 2017/0151069 | A1 * | 6/2017 | Geyer | A61F 2/70 |
| 2020/0315899 | A1 | 10/2020 | Takahashi et al. | |
| 2021/0059841 | A1 | 3/2021 | Goldfarb et al. | |

* cited by examiner

CONTROL METHOD FOR A POWERED KNEE ANKLE FOOT ORTHOSIS

This application is a national phase of International Application No. PCT/US2021/022287 filed Mar. 15, 2021, which is hereby incorporated herein by reference in its entirety.

FIELD OF INVENTION

The present application relates to mobility assistance devices, such as orthotic and prosthetic devices, and more particularly to an electronic control system and methods for a powered knee-ankle-foot orthosis.

BACKGROUND OF THE INVENTION

Many health conditions result in significant impairment to mobility, which may be associated with varying degrees of mobility impairment. The large population of persons afflicted with such conditions include, for example, those affected by stroke, multiple sclerosis, ALS, Parkinson's disease, spinal cord injury, cerebral palsy, amputees, and many other conditions resulting from birth defects, disease, injury, or aging. To aid mobility, mobility assistance devices, such as leg orthotic devices and prosthetic devices, have been employed.

Traditionally, the field of orthoses has specialized in highly custom, form-fitting braces that are made to fit the unique anatomy and needs of each individual patient. The simplest form of such a device is a passive or non-powered orthotic device with a long-leg brace that extends over the knee and incorporates an ankle-foot orthosis to provide support at the ankle, which is coupled with the leg brace to lock the knee joint in full extension (referred to in the art as a "knee-ankle-foot-orthosis" or "KAFO"). In another configuration, the leg brace further may be connected to a hip component that provides added support at the torso (referred to in the art as a "hip-knee-ankle-foot-orthosis" or "HKAFO"). To decrease the high level of exertion associated with passive orthoses, the use of powered mobility assistance devices has been under development, which incorporate actuators and drive motors associated with a power supply to assist with locomotion. These powered mobility assistance devices have been shown to increase gait speed and decrease compensatory motions, relative to walking without powered assistance. The use of powered mobility assistance devices presents an opportunity for electronic control of the mobility assistance devices for enhanced user mobility.

Human gait generally includes two main phases: a stance phase and a swing phase. The stance phase occurs during the time the foot is in contact with the ground, and the swing phase occurs during the time the foot is off the ground and the lower leg is swinging such as during stepping. These phases can further be broken down into intermediate states that together form a complete gait cycle. During gait, forces are generated on the human foot that that can be sensed by appropriate sensors incorporated into a foot plate component of a powered KAFO (or HKAFO) device. In addition, appropriate sensors in other components of a powered orthosis, such as for example in an actuator component that drives a joint component, can be used to measure such parameters as angular positions of portions or components of a powered orthosis (e.g., a flexion or extension angle of a lower leg assembly relative to a knee joint component; user tilt angles), as well as velocity measurements (e.g., velocity of rotation of a lower leg assembly about a knee joint during a gait swing phase). Such measurements can provide a basis for control of a powered orthosis that provides suitable mobility assistance in a manner that mimics human gait motion to the extent of a user's physical capabilities, although such control is difficult to implement and there remains room for enhancement and optimization of electronic control for a powered orthosis.

In a particular example of control issues, KAFO devices typically are prescribed for individuals with knee instability, quadriceps weakness, knee hyperextension, and varus or valgus deformity. In conventional passive KAFO devices, the knee joint is locked, which provides weight-bearing knee stability, enabling ambulation while precluding knee buckling. However, locking the knee joint results in loss of foot clearance during the swing phase of gait, and thus the user tends to compensate for the locked knee joint by deviating from typical gait motion, such as by circumduction, vaulting, and hip hiking.

In one variation of a KAFO device, referred to in the art as a "stance control KAFO" (SC-KAFO), the knee joint only is mechanically locked during the stance phase of gait, with the knee joint mechanically releasing during the swing phase to allow a freer swing for a more normal gait motion. Many SC-KAFO devices are limited to mechanically operated (i.e., non-electronic) knee-angle-dependent locking versus unlocking, which may be unreliable on certain terrains and unsuitable for users with substantial knee stability impairment. Such devices also commonly require ankle dorsiflexion or a knee extension moment to implement unlocking, resulting in unreliable disengagement of the lock resulting in a significant stumble risk. Such devices also are unable to provide active swing flexion or extension assistance to aid walking, and therefore SC-KAFOs are difficult to use by individuals with severe quadriceps weakness or limited hip flexion. Since conventional SC-KAFOs are mechanical locking devices that do not actively control the position of the knee joint and require full knee joint extension to lock, such devices often fail to provide reliable support for stance phase weight bearing.

Effective control is therefore deficient in the various types of conventional KAFO devices.

SUMMARY OF THE INVENTION

The present application describes a highly adaptable and adjustable control system and methods for a powered mobility assistance device, such as for example a powered knee-ankle-foot orthosis ("KAFO), which provides reliable knee support during the stance phase of gait, predictable motion during the swing phase of gait, and a high level of cooperation with the user's physical capabilities versus need for mobility assistance. Embodiments of the present application provide reliable stance phase knee joint locking at any suitable knee angle, reliable knee joint unlocking, and active or powered assistance for knee flexion and extension during the swing phase of the gait cycle. A powered KAFO implements electronically controlled swing assist and stance control instead of the conventional passive and mechanical locking control as described above.

Sensors within the powered KAFO device, which may be incorporated into an actuator assembly of the KAFO device, measure knee joint angle and knee joint rotation angular velocity, and thigh tilt relative to vertical. In addition, sensors embedded into the foot plate component of the KAFO measure heel and toe ground reaction forces. The sensor measurements are combined to provide a real-time determination of the user's current position and motion within a gait cycle, resulting in a robust degree of control that ensures accurate and reliable knee joint locking, knee joint unlocking, and swing phase initiation and assistance. The powered KAFO maintains locked knee joint support so long as the ground reaction force measurements for heel and toe are above an amount set for a specific user, indicating the stance phase of gait. When a user intends to take a step, i.e. initiating the swing phase of gait from the stance phase, the heel force measurement drops as measured by the sensors, and the knee joint lock releases to permit the stance phase. The system then initiates swing phase after a small amount of user-generated thigh tilt motion that indicates stepping initiation. During the swing phase, the powered KAFO device drives the lower leg assembly of the KAFO to rotate the user's lower limb into knee flexion and then into knee extension to assist stepping.

The powered KAFO is operable in at least three operating modes: walk mode, lock mode, and free mode. In walk mode the powered KAFO provides stance knee support and swing assist through multiple gait cycles associated with walking. Minimal user input is required beyond natural weight shifts and slight hip flexion that result in the sensor measurements referenced above. No additional manual user inputs, such as button pressing or mode switching, is needed for or during standing, level-ground walking, inclines, declines, stairs ascent or descent, side-shuffling, or stepping backwards. In the lock mode the powered KAFO maintains the knee joint component in a locked state and does not release the knee joint component regardless of user weight shifts or hip flexion. In the free mode the powered KAFO maintains the knee joint component in an unlocked state with the actuator assembly maintained inactive. Modes may be manually changed, and mode transitions also may be made by the powered KAFO automatically based on user positional changes.

Mode transitions may include the transition from free mode to walk mode after a sit-to-stand motion of the user is sensed, and as a transition from walk to free mode after a stand-to-sit motion of the user is sensed. The user may also adjust the level of active assistance provided by the powered KAFO during the swing phase of the gait cycle, for example by adjusting the target peak knee flexion angle with manual controls such as "+" and "−" buttons on a physical keypad for increased versus decreased powered assistance respectively. The electronic control system interface may employ multi-color LEDs to indicate whether the device is on, the current mode, level of active assistance, and battery state of charge of the device. The control system further may distinguish between minor and major stumbles and react to complete a step or lock of the knee joint component, respectively, to attempt stumble recovery. The electronic control system further prevents undesirable movement by monitoring the orientation of the user and ensuring steps are only able to be triggered in accordance with proper user positioning and while the user is upright.

The control system and related methods of operating a mobility assistance device provide an enhanced method of operating to better approximate a human gait cycle for enhanced mobility assistance. The device control includes performing a gait cycle including stance control of a knee joint component of the powered mobility assistance device during a stance substate of the gait cycle, and swing control of the knee joint component during a swing substate of the gait cycle, wherein multiple gait cycles of the stance control and the swing control are implemented for walking using the powered mobility assistance device. The stance control includes: reading a desired stance knee angle of the knee joint component that is preset into a control system of the powered mobility assistance device; detecting an actual stance knee angle of the knee joint component as measured by sensors in the powered mobility assistance device; and measuring an error between the desired stance knee angle and the actual stance knee angle, and when the error between the desired stance knee angle and the actual stance knee angle exceeds a threshold error, operating an actuator assembly of the powered mobility assistance device to control the knee joint component to stabilize the knee joint component during the stance substate of the gait cycle. The swing control includes: reading a desired swing knee trajectory of the knee joint component that is preset into the control system of the powered mobility assistance device, wherein a swing knee trajectory is defined as a pattern of knee flexion and extension of the knee joint component through the swing substate of the gait cycle; detecting an actual swing knee trajectory of the knee joint component as measured by the sensors in the powered mobility assistance device; and measuring an error between the desired swing knee trajectory and the actual swing knee trajectory, and operating the actuator assembly of the powered mobility assistance device to control the knee joint component to adjust the actual swing knee trajectory toward the desired swing knee trajectory during the swing substate of the gait cycle. The control method may be implemented by an electronic control system of the mobility assistance device executing a control application embodied as program code stored on a non-transitory computer readable medium.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

DETAILED DESCRIPTION

Figure 1:
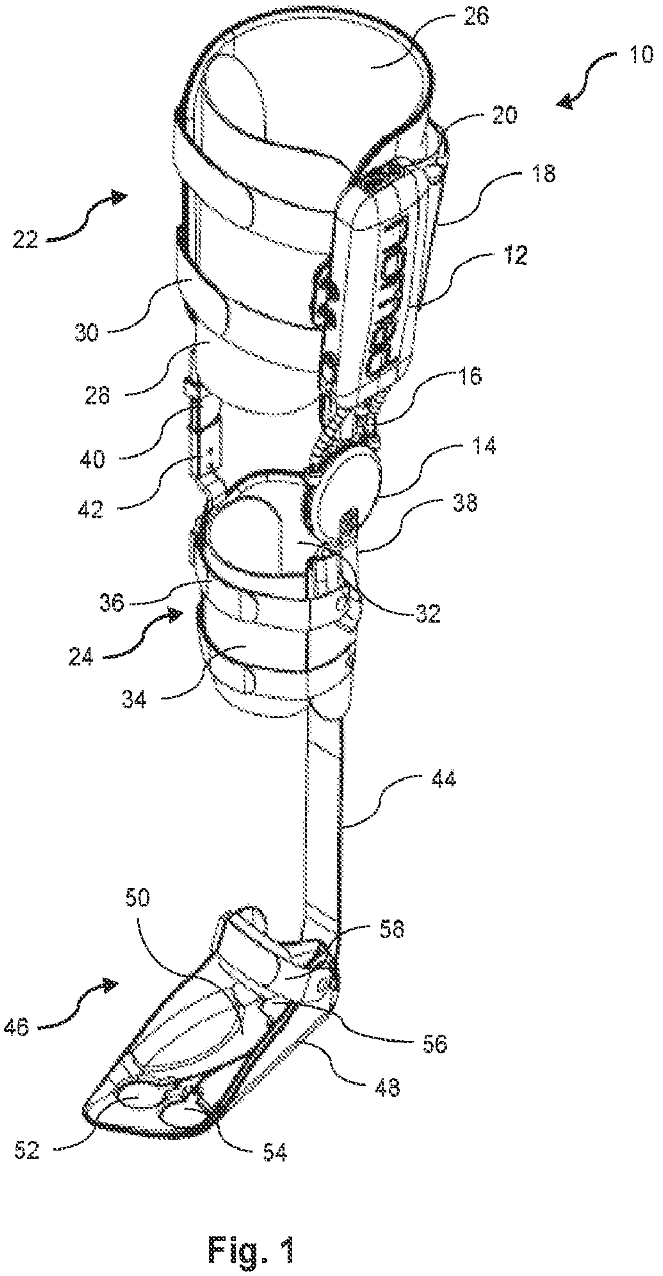
FIG. 1 is a drawing depicting an exemplary KAFO device in accordance with the present application.

Embodiments of the present application will now be described with reference to the drawings, wherein like reference numerals are used to refer to like elements throughout. It will be understood that the figures are not necessarily to scale.

The present application describes a highly adaptable and adjustable electronic control system and methods for a powered mobility assistance device, such as a powered orthosis configured as a knee-ankle-foot orthosis (KAFO), which provides reliable knee support during the stance phase of a gait cycle, predictable motion during the swing phase of the gait cycle, and a high level of cooperation with the user's physical capabilities versus need for mobility assistance. Embodiments of the present application provide reliable stance phase knee joint locking at any suitable knee angle, reliable knee joint unlocking, and active or powered assistance for knee flexion and extension during the swing phase of the gait cycle. A powered KAFO implements electronically controlled swing assist and stance control instead of the conventional passive and mechanical locking control as described above in the background section.

FIG. 1 is a drawing depicting an exemplary KAFO device 10 in accordance with the present application. Although the principles of this invention are described largely in connection with a KAFO device, comparable principles are applicable to any suitable powered mobility assistance device, including for example a powered hip-knee-ankle-foot orthosis (HKAFO) device. The configuration of the KAFO device represents a suitable example for implementing the electronic control system and methods of the current application, although it will be appreciated that variations in the physical structure of the KAFO 10 may be employed while still accommodating such electronic control system and methods.

As a depicted example, the KAFO device 10 includes an actuator assembly having an actuator 12 that drives a knee joint component 14 via drive cables 16, whereby the knee joint component is rotatable to drive rotation of a lower leg assembly relative to an upper leg assembly of the KAFO. As further detail below, the actuator 12 includes a motor whose output is modified by a transmission system, wherein motion is imparted from the actuator 12 via the drive cables 16 to drive rotation of the knee joint component 14. The actuator 12 further may include a brake for damping the motor output, and various sensor and control electronics for implementing the enhanced KAFO control as described below. The actuator 12 is powered by a detachable battery pack 18, which may be removed for recharging and/or replacement by another comparable battery pack. The actuator 12 further may include a user interface 20, which may include manual control buttons and visual indicators that indicate the state or mode of the KAFO (for example using LEDs).

The KAFO 10 may include an upper leg assembly 22 and a lower leg assembly 24. The actuator 12 is mounted to the upper leg assembly 22 by any suitable mechanism. The upper leg assembly 22 may include a thigh shell 26, which may be made of a carbon fiber material and supports a user's upper leg just above the knee. The upper leg assembly further may include a thigh tongue 28 positioned forward relative to the thigh shell 26. The upper leg assembly 22 further may include an upper attachment device 30 to secure the KAFO 10 to the user's upper leg or thigh. For example, the upper attachment device 30 may include a series of adjustable straps that are secured using a hook-loop type fastening mechanism. The thigh tongue 28 may be made of a semi-flexible plastic material that distributes compression from the upper leg straps about the user's thigh when the KAFO is worn. Similarly, the lower leg assembly 24 may include a lower leg shell 32, which also may be made of a carbon fiber material and supports a user's lower leg just below the knee. The lower leg assembly 24 further may include a lower leg tongue 34 positioned forward relative to the lower leg shell 32. The lower leg assembly further may include a lower attachment device 36 to secure the KAFO 10 to the user's lower leg. For example, the lower attachment device 36 also may include a series of adjustable straps that are secured using a hook-loop type fastening mechanism. The lower leg tongue 34 also may be made of a semi-flexible plastic material that distributes compression from the lower leg straps about the user's lower leg when the KAFO is worn.

The lower leg assembly 24 is attached to the upper leg assembly 22 by a first attachment bar 38 and a second attachment bar 40. The first attachment bar 38 is fixed to the knee joint component 14 by any suitable means, such as using bolts or screws. Accordingly, the first attachment bar 38 will swing as the knee joint component 14 rotates. The second attachment bar 40 is fixed at a first end to the upper leg assembly and at a second to the lower leg assembly, also by any suitable means such as bolts or screws. The second attachment bar 40 has a hinge connection 42 that permits rotation of the second end relative the first end. With such connection of the upper leg assembly and the lower leg assembly via the two attachment bars, when the knee joint component 14 rotates the entire lower leg assembly 24 swings or rotates via the knee joint component 14 relative to the upper leg assembly 22.

The lower leg assembly further includes a lower bar 44 that extends down from the lower leg shell 32 to an ankle-foot component 46. The ankle-foot component 46 includes a foot plate 48, which may be made of a comparable material as the thigh and lower leg shells and provides a support structure for the user's foot and ankle. The ankle-foot component 46 further may include a sensor insole 50, which may be made of a compressible material such as a foam or gel encased in plastic. The sensor insole 50 may include foot sensors that can detect ground forces when a user's body weight is applied to the foot during use. For example, the foot sensors include a medial toe sensor 52, a lateral toe sensor 54, and a heel sensor 56. This three-sensor configuration has been determined to be suitable for implementing the control described in the current application, although other foot sensor configurations may be employed. The ankle-foot component 46 further may include a foot attachment device 58 to secure KAFO 10 to the user's foot and ankle during use, which also may include an adjustable strap that is secured using a hook-loop type fastening mechanism.

Figure 2:
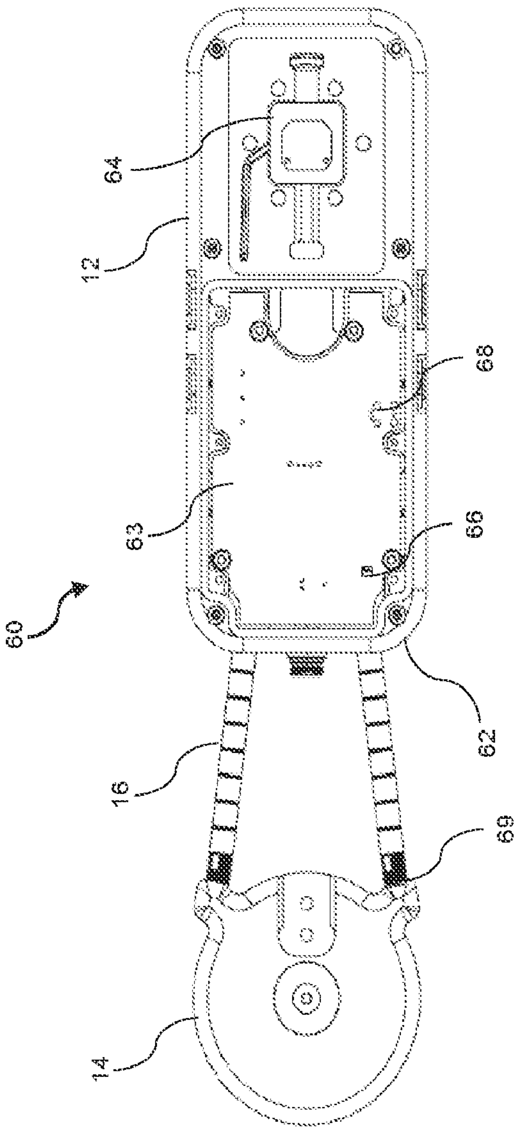
FIG. 2 is a drawing depicting a top view of an exemplary actuator assembly in accordance with the present application.

FIG. 2 is a drawing depicting a top view of an actuator assembly 60 in isolation that may be used in the KAFO of FIG. 1. Referring to FIG. 2 in combination with FIG. 1, the overall actuator assembly 60 includes the actuator 12 connected to the knee joint component 14 via the drive cables 16 as referenced above, and thus like reference numerals are used in FIG. 2 as in FIG. 1. The actuator 12 has an actuator housing 62 for housing the various actuator components, and in the depiction of FIG. 2, a portion of the actuator housing 62 is removed to illustrate the internal electronics housed within the actuator housing. The internal electronics may include a sensor and control circuit board 63 and an electronic control system 64. The circuit board 63 may incorporate electronic sensors for sensing parameters associated with electronic control of the KAFO. The electronic sensors may be incorporated into an integrated circuit chip, referred to as an inertial measurement unit (IMU) 66 for sensing tilt measurements and related motions and positioning of the user's body relative to the legs. Examples sensors that may be incorporated into the IMU more generally may include accelerometers, gyroscopes, inertial measurement sensors, hall effect sensors, magnetic angle sensors, resistance temperature detectors, and other sensors to detect and observe the leg and torso orientation or angle and angular velocity of the knee joint component. Typically, the IMU 66 at least would incorporate a gyroscope that measures an angular velocity, such as the rotation of the knee joint component, and an accelerometer that measures tilt of the actuator assembly relative to vertical or gravity. There also may be one or more redundant sensors that correspond respectively to one or more of the above sensors, and the redundant sensors may provide sensor information when there is a sensor fault detected in a respective sensor. The circuit board 63 also may include an additional dedicated accelerometer chip 68 that particularly can sense flexion and extension angles of the knee joint component 14 in addition to tilt measurements as referenced above. As further detailed below, the electronic control system 64 receives sensor information from the IMU 66 and the accelerometer 68, and also from the foot sensors (e.g., foot sensors 52, 54, and 56). Based on the received sensor signals, the electronic control system 64 operates the actuator motor and brake to control rotation of the knee joint component. The actuator assembly 60 further may include tensioners 69 for adjusting or tightening the tension in the drive cables 16.

Figure 3:
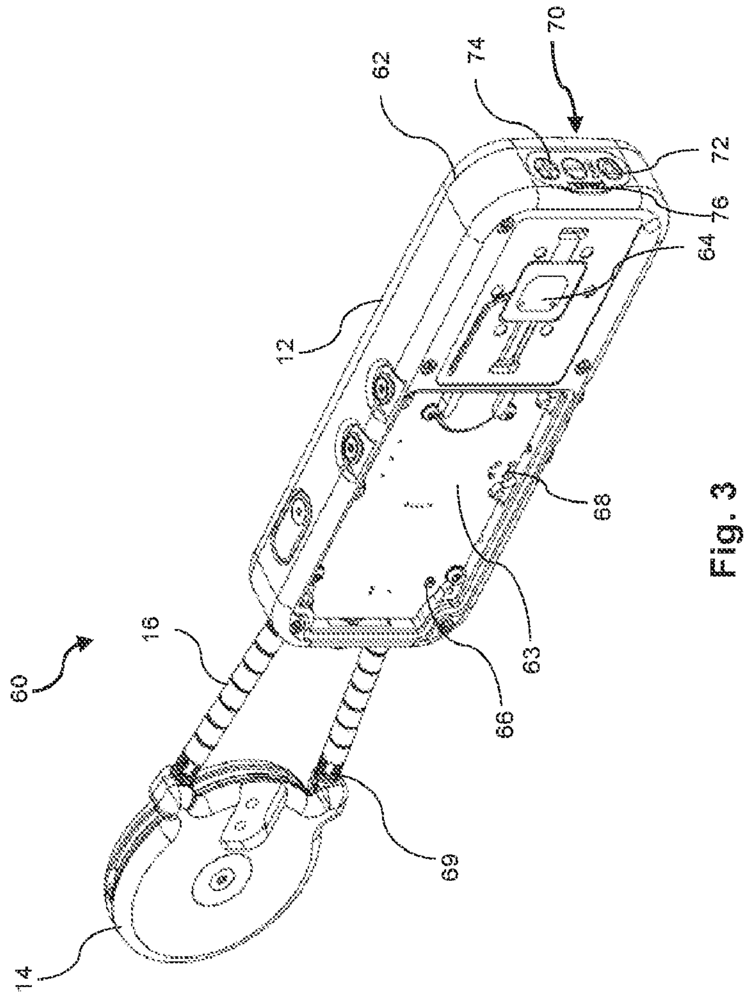
FIG. 3 is a drawing depicting a perspective view of the exemplary actuator assembly of FIG. 2.

FIG. 3 is a drawing depicting a perspective view of the exemplary actuator assembly 60 of FIG. 2. The viewpoint of FIG. 3 in particular illustrates an exemplary user interface 70. The user interface 70 may permit simple user input commands, such as for example a mode button 72 that can power-on the KAFO device and be pressed to manually transition between different modes of operation, and "+" and "−" command buttons 74. The command buttons 74 may be used, for example, to increase or decrease a level of mobility assistance to be provided by the actuator assembly 60 during a swing phase of a gait cycle, which can be varied as warranted based on the user's mobility capabilities. The user interface 70 also may include visual indicators 76, such as LEDs, that may light up and/or light up in different colors and/or at different on/off rates (e.g., solid on/off versus blinking) to convey different states or modes of the KAFO, indicate the on/off state of the device, provide device alerts or warnings, and indicate the battery level.

Figure 4:
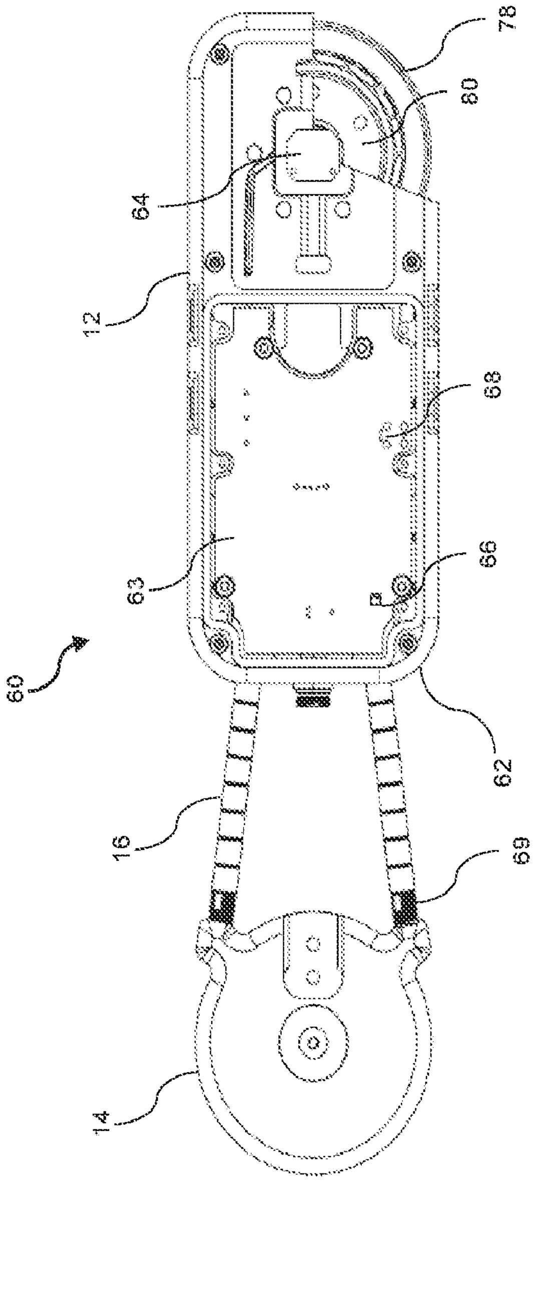
FIG. 4 is a drawing depicting the top view of the exemplary actuator assembly of FIG. 2, with an additional cutaway for illustrating certain internal components.

FIG. 4 is a drawing depicting the top view of the exemplary actuator assembly 60 of FIG. 2, with an additional cutaway for illustrating certain additional internal components. The actuator 12 further includes a motor 78 and a brake 80 as referenced above for controlling the driving and braking of the knee joint component 14. The output of the motor may be modified by a speed reduction transmission component of the actuator 12, with motion being transmitted via the drive cables 16 to rotate the knee joint control component 14.

Figure 5:
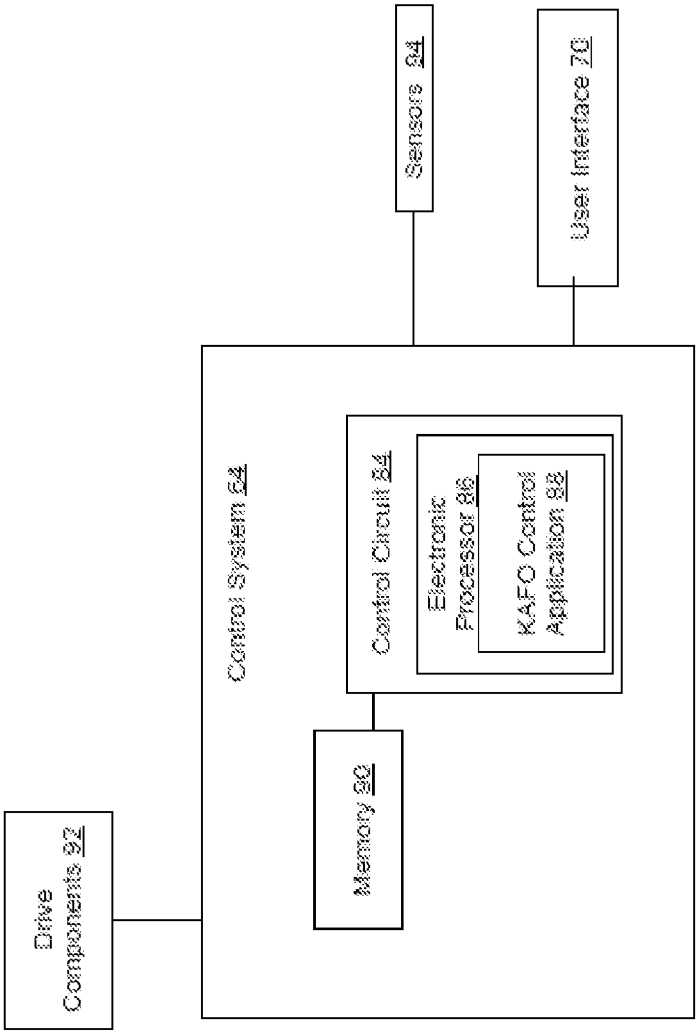
FIG. 5 is a drawing depicting a schematic block diagram of operative portions of the exemplary control system and related electronic components that control the actuator assembly.

FIG. 5 is a drawing depicting a schematic block diagram of operative portions of an exemplary configuration of the electronic control system 64 and the related electronic components. The electronic control system 64 may include a primary control circuit 84 that is configured to carry out various control operations relating to control of the KAFO device. The control circuit 84 may include an electronic processor 86, such as a CPU, microcontroller or microprocessor. Among their functions, to implement the features of the present invention, the control circuit 84 and/or electronic processor 86 may execute program code embodied as a KAFO control application 88. It will be apparent to a person having ordinary skill in the art of computer programming, and specifically in application programming for electronic and communication devices, how to program the device to operate and carry out logical functions associated with the control application 88. Accordingly, details as to specific programming code have been left out for the sake of brevity.

The KAFO control application 88 may be stored in a non-transitory computer readable medium, such as a random access memory (RAM), a read-only memory (ROM), an erasable programmable read-only memory (EPROM or Flash memory), or any other suitable medium. In the example of FIG. 5, the KAFO control application 88 is shown as being stored internally within the processing components, but the control application also may be stored in an additional memory device such as the memory 90. Instructions for performing device control that are stored in the non-transitory computer readable medium may be executed by the processor components 84 and 86. Such controller functionality could also be carried out via dedicated hardware, firmware, software, or combinations thereof, without departing from the scope of the invention.

The electronic control system 64 further may be in electronic communication with both the sensory and drive components of the KAFO device. The connections may be hard wired connections through the KAFO structure and via the internal circuit board 63, and wireless communication also may be employed between the control system and/or sensor components when appropriate, particularly for example for communication with the foot sensors 52, 54, and 56 that are more remote from the actuator assembly. As referenced above, sensor information also is received by the electronic control system 64 from the sensors electronically integrated within the circuit board 63, such as for example the IMU 66 and the accelerometer 68. In FIG. 5, all such sensors are simply denoted generally as element 94. The electronic control system 64 may then selectively control the drive components, referred to generally with reference numeral 92. The drive components may include the motor 78 and associated speed reduction transmission, and the brake 80 referenced above, which in turn ultimately control rotation of the knee joint component 14 to apply torque for mobility assistance or joint resistance, implement locked or released states of the knee joint component, or otherwise implement positioning or movement of the knee joint component for various modes of operation, and for stumble recovery, fall mitigation, and other control operations as detailed below.

The electronic control system 64 further may be in electronic communication with the user interface 70, including the mode and command buttons 72 and 74, and the visual indicators 76 described above. The visual indicators may indicate aspects of device state and operation by lighting, such as by color-coded lighting in which light emitting diodes (LEDs) are employed as the visual indicators 76. Additional indicators may be employed, such as for example audio indicators by which speakers may be employed to provide audio alerts pertaining to aspects of device state and operation.

In general, the sensors within the actuator assembly measure knee joint angle and thigh tilt relative to vertical, as well as angular velocity of the knee joint component. In addition, the sensors embedded into the foot plate component of the KAFO measure heel and toe ground reaction forces. The sensor measurement signals together provide a real-time determination of the user's current position and motion within the gait cycle, resulting in a robust degree of control that ensures accurate and reliable knee joint locking, knee joint unlocking, and swing phase initiation and powered assistance. The powered KAFO 10 is operable in at least three operating modes that are designated as the walk mode, lock mode, and free mode. Transitions between these modes may be manually performed by the user, such as for example by pushing the mode button 72 of the user interface 70, and/or transitions between these modes may be performed automatically based on user positional changes as determined by the electronic control system 64 based on the sensor signal information.

In free mode, the control system operates to maintain the knee joint component in an unlocked state with the actuator being maintained inactive. Free mode permits the user to manually adjust the knee joint component without resistance or assistance by the powered actuator assembly. The knee joint component becomes completely passive during this mode, and due to the actuator assembly's high back-drivability, the position of the knee joint component can easily be adjusted by user motion. Accordingly, a user may walk without powered assistance similarly as with a passive KAFO device, which can help a user build strength and capability. If a manual lock is present on the KAFO as is common in conventional KAFO devices, entering free mode may be used to manually position the knee joint component so that the manual lock may be engaged to maintain the user's knee in a particular position.

In lock mode, the control system operates to maintain the knee joint component in a locked state and does not release the knee joint component regardless of how a user shifts weight or a degree of hip flexion. Lock mode creates very high resistance to motion of the knee joint component by engaging the brake to substantially resist knee joint component rotation. Regardless of user limb motion or tilt while in the lock mode, the control system does not disengage the brake. By engaging the brake to substantially resist knee joint component rotation, lock mode is well-suited to tasks in which stance support is desired for extended periods, but swing behavior is unnecessary, such as activities that may require substantial periods of standing. Lock mode also can provide a stable starting state in a stance position for transition from standing to walking in the walk mode.

In walk mode the control system operates to provide stance knee support and swing assist through multiple gait cycles associated with walking. Minimal user input is required beyond natural weight shifts and slight hip flexion that result in the sensor measurements described above. No additional manual user inputs, such as button pressing or mode switching, is needed for or during level-ground walking, inclines, declines, stairs ascent or descent, side-shuffling, or stepping backwards. In general, in walk mode the electronic control system operates to maintain locked knee joint component support so long as the ground reaction force measurements for heel and toe indicate the stance phase of a gait cycle. When a user positions to take a step, i.e. positions for initiating the swing phase of the gait cycle from the stance phase, the heel force measurement drops and the electronic control system operates to release the knee joint component for the locked state to permit proceeding to the swing stance phase. The control system then operates the knee joint component to initiate swing phase after a small amount of user-generated thigh tilt motion is detected to indicate step initiation. During the swing phase, the control system operates to drive the knee joint component such that the lower leg assembly of the KAFO rotates the user's lower limb into knee flexion and then into knee extension to provide powered assistance for walking.

Walk mode is subdivided into multiple substates as further detailed below. Transitions among these substates occur automatically as the user walks with the assistance of the KAFO device. The substates combine together to form a gait cycle through stance and swing portions of a gait cycle that may be repeated over multiple cycles for continuous walking. The walk mode thus corresponds to an enhanced method of operating a powered mobility assistance device to better approximate a human gait cycle for enhanced mobility assistance. In general, the walk mode includes performing a gait cycle including stance control of a knee joint component of the powered mobility assistance device during a stance substate of the gait cycle, and swing control of the knee joint component during a swing substate of the gait cycle, wherein multiple gait cycles of the stance control and the swing control are implemented for walking using the powered mobility assistance device.

The stance control includes: reading a desired stance knee angle of the knee joint component that is preset into a control system of the powered mobility assistance device; detecting an actual stance knee angle of the knee joint component as measured by sensors in the powered mobility assistance device; and measuring an error between the desired stance knee angle and the actual stance knee angle, and when the error between the desired stance knee angle and the actual stance knee angle exceeds a threshold error, operating an actuator assembly of the powered mobility assistance device to control the knee joint component to stabilize the knee joint component during the stance substate of the gait cycle. The swing control includes: reading a desired swing knee trajectory of the knee joint component that is preset into the control system of the powered mobility assistance device, wherein a swing knee trajectory is defined as a pattern of knee flexion and extension of the knee joint component through the swing substate of the gait cycle; detecting an actual swing knee trajectory of the knee joint component as measured by the sensors in the powered mobility assistance device; and measuring an error between the desired swing knee trajectory and the actual swing knee trajectory, and operating the actuator assembly of the powered mobility assistance device to control the knee joint component to adjust the actual swing knee trajectory toward the desired swing knee trajectory during the swing substate of the gait cycle. The control method may be implemented by the electronic control system of the mobility assistance device executing the control application embodied as program code stored on the non-transitory computer readable medium.

As referenced above, the first substate to be described is referred to as the stance substate. For illustrative purposes it is reasonable to describe the stance substate first in relation to the other substates of the walk mode. For safety and efficiency, transitions into walk mode from a previous free or lock mode typically place the KAFO device in the stance substate of the walk mode so that the user commences walking from the stable standing position corresponding to the stance portion of the gait cycle.

Figure 6:
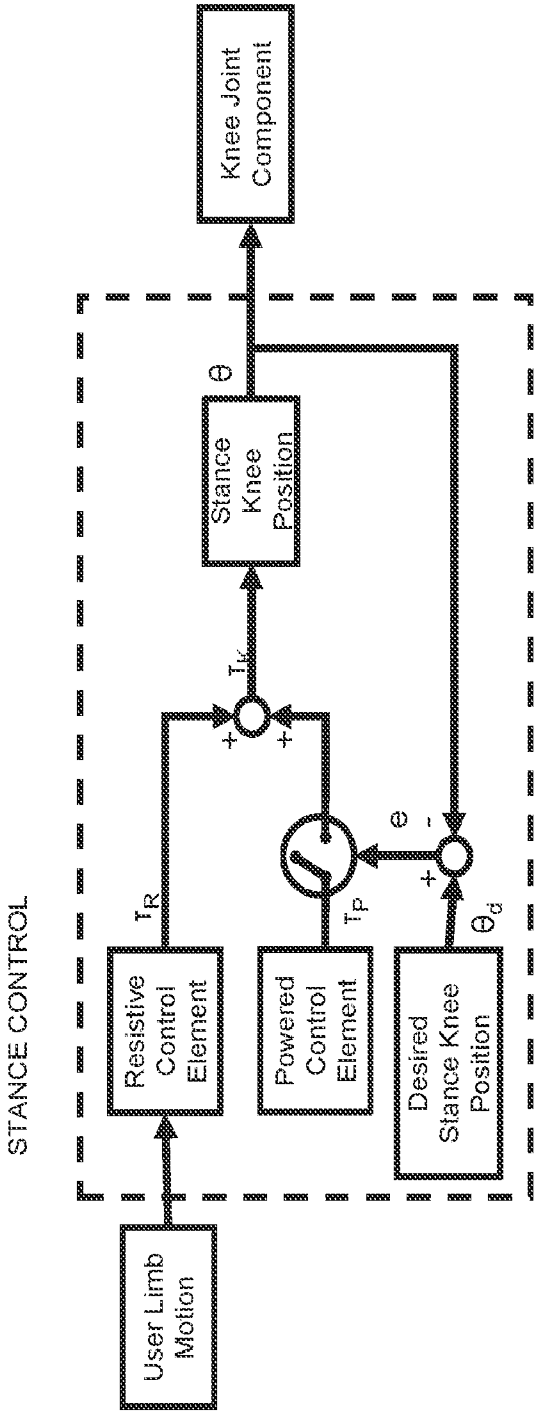
FIG. 6 is a drawing depicting a block diagram illustrating stance control implemented by the electronic control system during the stance substate within a gait cycle.

FIG. 6 is a drawing depicting a block diagram illustrating stance control implemented by the electronic control system during the stance substate. As seen in FIG. 6, for stance control the electronic control system receives an input of limb motion as measured by the various sensors described above. The electronic control system is configured to operate a resistive control element to provide resistance to knee joint component motion, for example by engaging the brake. The electronic control system also is configured to operate a powered control element to provide additional resistance or mobility assistance to knee joint component motion, for example by controlling the actuator assembly to further resist or assist joint rotation of the knee joint component.

In the stance substate, the electronic control system provides a high resistive control element whereby the KAFO device brake is engaged to provide high resistance to flexion of the knee joint component ($T_R$). The stance substate essentially corresponds to standing, and thus all the pressure sensors in the foot plate are highly or fully loaded. To maintain a stance position, high resistance to knee flexion stabilizes the knee joint component to maintain balance during standing. Because the KAFO brake is a friction brake (as opposed to a mechanical lock), however, it is possible for the knee joint component to slip under heavy load conditions. Accordingly, the electronic control system reads a desired stance knee position ($\theta_d$) of the knee joint component, which is a parameter that is programmed or preset set into the control system as optimal for a particular user. The electronic control system also detects the actual stance knee position ($\theta$) of the knee joint component, as measured by the sensors of the KAFO device.

As shown in FIG. 6, slipping is detected by measuring an error (e) between the desired stance knee position ($\theta_d$) and the actual knee angle position ($\theta$) as determined by the KAFO position from the sensors. When the error reaches a threshold error of a deviation of the actual knee position relative to the desired stance knee position, the error is indicative that slipping is occurring. Under such circumstances of slipping, the resistance ($T_R$) provided by the resistive control element (brake) is insufficient for full stabilization of the knee joint component. Accordingly, the control system operates the actuator to control the knee joint component to supplement the resistance provided by the resistive control element with a powered control element ($T_P$) to better stabilize the knee joint component during the stance substate of the gait cycle. For example, the electronic control system may provide additional resistance via powered actuation of the actuator assembly to provide ($T_P$). The KAFO device is highly sensitive to the detection of slipping during the stance substate. Because the transmission reduction of the actuator assembly can be around 22:1 (or more), this means that a one-degree error in the actual knee angle position relative to the desired knee angle position is equivalent to a 22° spin at the motor. Accordingly, the threshold error to trigger application of ($T_P$) by the powered control element (actuator) typically can be less than one degree. In exemplary embodiments, the threshold error is in a range from 0.1 degree to two degrees.

As referenced above, when the threshold error (e) is sufficient to indicate non-negligible slipping, the control system operates the actuator to control the knee joint component to further stabilize the knee joint component during the stance substate of the gait cycle. For example, the electronic control system may provide additional resistance via powered actuation of the actuator assembly ($T_P$). In FIG. 6, this operation is illustrated schematically as a switch which closes in response to the threshold error being satisfied to impart operation of the powered control element to add the additional resistance. The powered control element ($T_P$) is combined with the resistive control element ($T_R$) into a total output torque ($T_K$) to provide adequate resistance to knee flexion of the knee joint component to stabilize the knee joint component during the stance substate. If slipping is occurring regularly during gait, the electronic control system increases the powered control element contribution to increase the amount of resistive torque provided by the actuator assembly. In contrast, if numerous steps are taken without detecting brake slip, the electronic control system will reduce or eliminate the amount of torque provided by the actuator assembly (i.e., the switch in FIG. 6 will be open as shown), which reduces the battery draw so that less power is used when no slipping is detected.

The next substate of the walk mode is referred to as the neutral substate, which is a transition from the stance substate to the swing substate. When a user begins to initiate stepping, the input received corresponding to the user limb motion measurement changes. In particular, the pressure sensors in the foot plate of the KAFO transition from being highly loaded toward being unloaded as the user's foot begins to raise from the ground. The neutral substate thus is a brief substate that corresponds to a transition out of the stance substate. In the neutral substate, in response to the transition toward unloading of the pressure sensors in the foot plate, the electronic control system renders inactive both the resistive control element and the powered control element, such as by disengaging the brake and providing zero torque from the actuator assembly (i.e., both the resistive control element $T_R$ and the powered control element $T_P$ in FIG. 6 are taken to zero). This permits the user to begin "breaking" the knee, i.e., unlocking the knee from the rigidity associated with standing into flexion, prior to lower leg swing initiation. The neutral substate, therefore, constitutes a transitional state in which stance support is no longer provided but swing has not yet been initiated. If the electronic control system detects that the limb motion indicates a return to loading of the pressure sensors of the foot plate, which indicates that the user is to remain standing, then the electronic control system returns to the KAFO to the stance substate. Otherwise, electronic control for the swing substate of the gait cycle proceeds.

There may be variations in the manner by which the electronic control system transitions into the neutral substate from the stance substate. One such variation is in the timing of the release of the knee joint component support for transition from the stance substate into the neutral substate. Depending upon the level of instability in a user's stance knee, the user may require that the electronic control system release stance support (i.e. enter the neutral substate) at different points during the stance substate. For users with moderate knee joint control, it is preferable that the electronic control system releases the stance knee support during the stance substate when it is detected from the pressure sensors that the center of pressure of a user's foot has advanced from the heel of the foot to the ball of the foot. This permits the user to break the knee in anticipation of toe-off and swing initiation. On the other hand, for users with little to no knee joint control, it is preferable that the electronic control system releases the stance knee support later to maintain stance support through the terminal or end of the stance substate, and release the knee support only when the user's weight is essentially fully off of the foot.

This occurs when it is detected from the foot pressure sensors that the pressure sensors are fully (or nearly fully) unloaded. The electronic control system permits a programmed selection to be entered for operation of either stance support release occurring at heel off (i.e. when the user's weight is no longer detected on the heel, but may still be present on the toe) or toe off (i.e. when the user's weight is no longer detected on either the heel or the toe). In both cases, the heel and toe pressure sensors are loaded between steps to ensure that a full stance substate has occurred prior to entering a new neutral substate in preparation for entering a new swing substate.

Another such variation is an adjustment of a step trigger for transition from the neutral substate to the swing substate of the gate cycle associated with stepping. As referenced above, users with lower limb impairment will often have developed compensatory strategies to enable walking with a conventional passive KAFO. For example, users who walk with a locked-knee KAFO often circumduct their braced leg, while others "vault" by excessively plantarflexing the contralateral ankle or "hip hike", all to elevate the braced-side foot and achieve foot clearance for stepping. Because the lower-limb movement pattern produced by these strategies vary widely, the electronic control system detects these various swing-initiation patterns so that the swing phase is initiated with a correct timing. With use of the powered KAFO device of the present application over time, such compensatory strategies should reduce and become eliminated as the user becomes accustomed to the more natural gait cycle of the powered KAFO device. A step trigger may be programmed into the electronic control system by an orthotist, and step trigger control further may be automatically adjusted by the electronic control system as the user capabilities improve versus the step trigger initially programmed by the orthotist.

Figure 7:
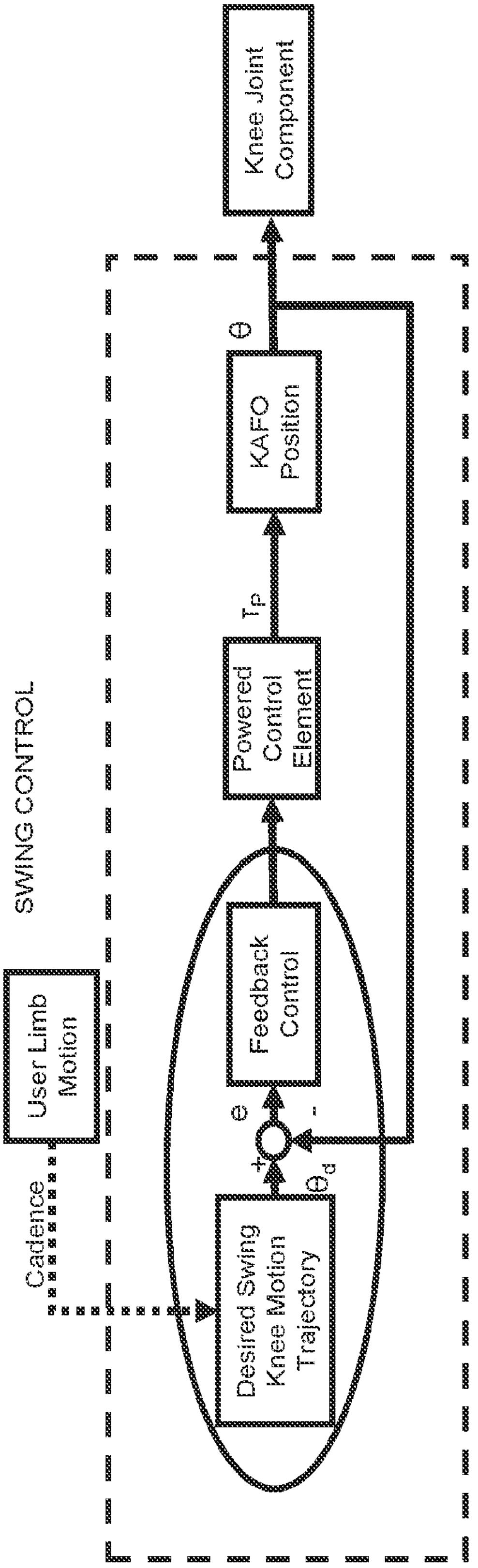
FIG. 7 is a drawing depicting a block diagram illustrating swing control implemented by the electronic control system during the swing substate within a gait cycle.

A user begins the swing phase of a gait cycle by transitioning from the neutral substate into the next substate corresponding to the initiation of a step. FIG. 7 is a drawing depicting a block diagram illustrating swing control implemented by the electronic control system during the swing substate of a gait cycle. As seen in FIG. 7, similarly as for stance control, for swing control the electronic control system receives an input of limb motion as measured by the various sensors described above. The electronic control system is configured to operate the powered control element to provide mobility assistance to knee joint component motion, for example by controlling the actuator assembly to assist knee joint component rotation during the swing substate of the gait cycle to assist the user's stepping motion. As referenced above, a level of assistance can be adjusted to be increased or decreased, such as by using the +/− command buttons of the user interface.

During the swing substate of the gait cycle, the knee joint component rotates through a swing knee trajectory that is defined as a pattern of knee flexion and extension through the swing substate of the gait cycle corresponding to a step. In general, as illustrated in FIG. 7, swing control is implemented by reading a desired swing knee motion trajectory ($\theta_d$) of the knee joint component, which also is a parameter that is programmed and preset into the control system as optimal for a particular user. The electronic control system also detects the actual swing knee trajectory of the knee joint component ($\theta$) based on the knee angle KAFO position at any given point in the swing phase as measured by the sensors of the KAFO device. As shown in FIG. 7, for any given knee angle position at a given point in the swing knee trajectory, the electronic control system measures the error (e) between the desired swing knee trajectory ($\theta_d$) and the actual swing knee trajectory ($\theta$) as determined from the KAFO position from the sensors. Depending upon the determined error, the electronic control system through feedback control provides mobility assistance via powered actuation of the actuator assembly ($T_P$) to correct the error in the swing knee trajectory. In this manner, the control system operates the actuator assembly to control the knee joint component to adjust or adapt the swing knee trajectory from the actual swing knee trajectory toward the desired swing knee trajectory during the swing substate of the gait cycle. Operating the actuator assembly in the swing control can be implemented by operating the powered control element to assist rotation of the knee joint component to provide an output torque (Tp) to rotate the knee joint component to adjust or adapt the swing knee trajectory toward the desired swing knee trajectory during the swing substate.

Figure 8:
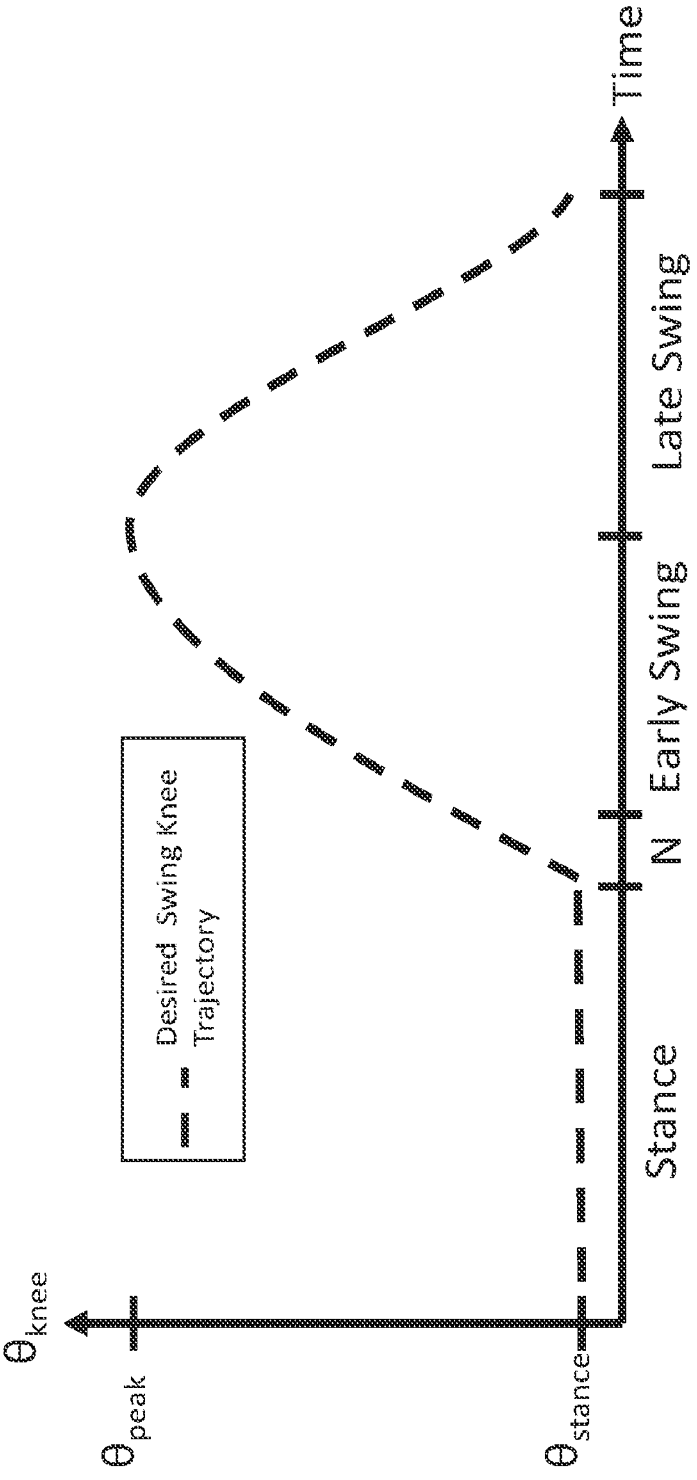
FIG. 8 is a drawing depicting an exemplary desired swing knee trajectory during an overall swing substate.

FIG. 8 is a drawing depicting an exemplary desired swing knee trajectory, which as referenced above can be programmed or preset into the control system as may be suitable for any particular user or circumstances. As referenced above, in general a swing knee trajectory is defined as a pattern of knee flexion and extension through the swing substate of the gait cycle corresponding to a step. In the desired swing knee angle trajectory of FIG. 8, the knee angle of the knee joint component begins at the stance knee angle $\theta_{stance}$ from the previous stance substate, and during the neutral substate (N) the user "breaks" the knee and the knee joint component transitions into flexion. During a first portion of the swing substate, referred to as the early swing substate, the knee joint component proceeds with increasing flexion until reaching a desired peak knee angle $\theta_{peak}$. After reaching the desired peak knee angle is a second portion of the swing substate, referred to as the late swing substate. At the peak knee angle, the knee joint component transitions from flexion to extension, corresponding to a transition from the early swing substate to the late swing substate. The knee joint component continues to extend through the late swing substate until the knee joint component returns to the desired stance knee angle, corresponding to the end of the swing substate and the beginning of the next stance substate. As referenced above, when an error is measured in the actual swing knee trajectory relative to the desired swing knee trajectory, the electronic control system operates the actuator assembly to control the knee joint component to adjust the swing knee trajectory from the actual swing knee trajectory toward the desired swing knee trajectory during the swing substate of the gait cycle.

Referring to such control in connection with specific substates of the walk mode, following the brief neutral substate the next substate of the walk mode is the early swing substate, which corresponds to the first portion of the overall swing substate of a gait cycle that principally is characterized by knee flexion of the knee joint component. The electronic control system enters the early swing substate when it is detected from the user limb motion that the user's limb initiates a forward swing, as measured by one or more of the accelerometer, gyroscope, and/or other sensors in the inertial measurement unit (IMU). During the early swing substate, the electronic control system guides the knee joint component along a variable trajectory using position and velocity control through a first portion of a step characterized principally by knee flexion. A knee swing trajectory error particularly can occur due to a variation in the knee angle of the knee joint component at the initiation of the early swing substate, or in FIG. 8 as an error in the beginning stance knee angle $\theta_{stance}$. Such variation in knee angle at early swing initiation is especially dominant during the initial transition from the neutral substate into the early swing substate because as referenced above, during the neutral substate the resistive control element and the powered control element are taken to zero (and thus the KAFO is not actively controlling the knee angle during the neutral substate).

Figure 9:
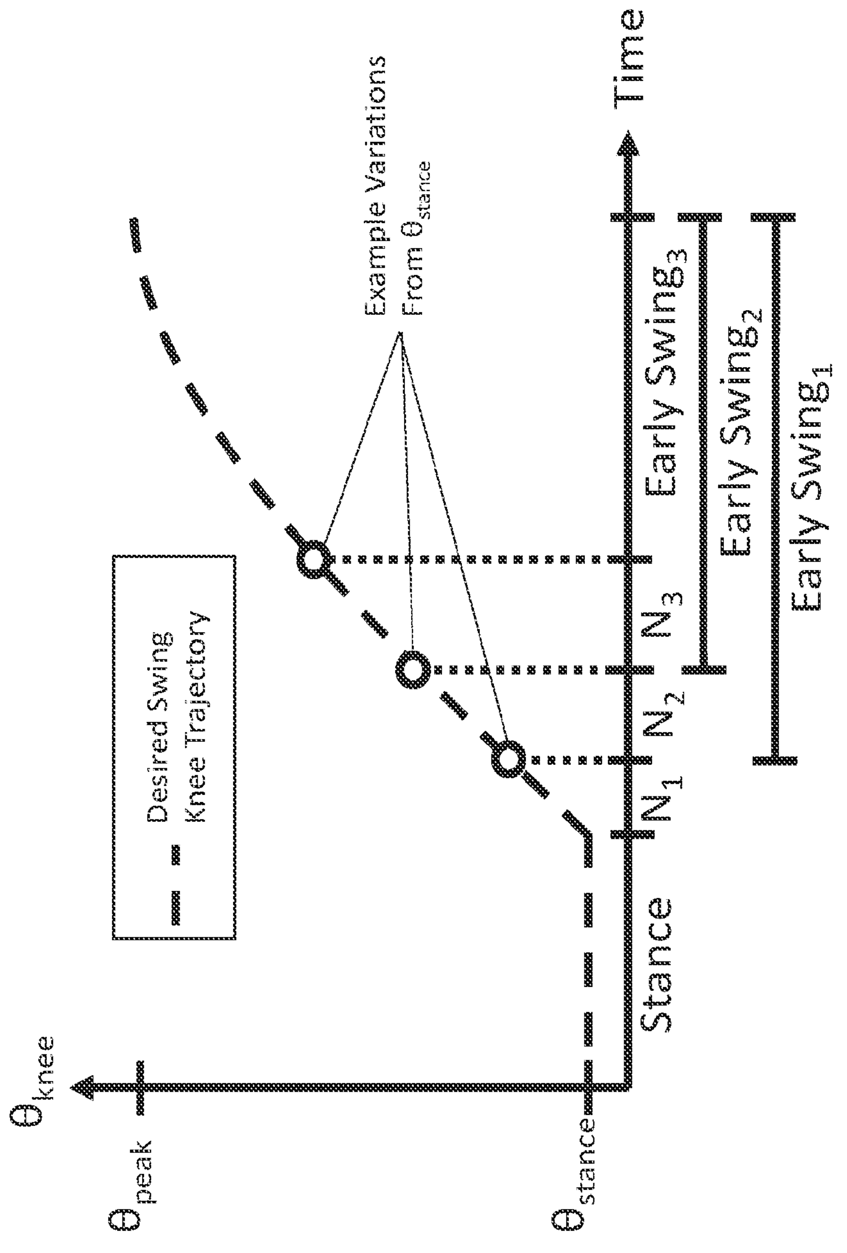
FIG. 9 is a drawing depicting an exemplary trajectory adaptation based on a first error correction during an early swing substate.

Referring first to FIG. 7 in combination with FIG. 8, the electronic control system reads the desired knee swing trajectory stored in the system, including reading the desired initial stance knee angle, and detects the actual swing knee trajectory including the actual initial stance knee angle. The electronic control system then measures a first swing error between the desired swing knee trajectory and the actual swing knee trajectory at the initiation of the early swing substate. The first error can be based on the actual knee angle of the knee joint component at the initiation of the early swing substate which results in the error relative to the desired swing knee trajectory at $\theta_{stance}$. In addition, FIG. 9 is a drawing depicting an exemplary trajectory adaptation during the early swing substate. FIG. 9 illustrates that the initial stance knee angle at the onset of early swing can vary from the desired stance knee angle $\theta_{stance}$ (three example variations are shown for illustration), which typically occurs as the knee joint component breaks during the neutral substate. This results in essentially a premature flexing of the knee joint component from the desired stance knee angle $\theta_{stance}$.

Looking at the graph of FIG. 9, this premature knee flexion results in the early swing substate initiating from a different location along the swing knee trajectory relative to the desired initiation location at $\theta_{stance}$. Accordingly, the electronic control system adapts the swing knee trajectory by implementing the swing knee trajectory from the point of the actual knee angle position rather than from the desired stance knee angle position $\theta_{stance}$. Essentially, the first part of the desired early swing knee trajectory is truncated from the desired stance knee angle position to the actual knee angle position at the onset of early swing. Referring back to FIG. 7, the error in particular is corrected according to feedback control via the operation of the powered control element ($T_P$) to provide mobility assistance with the actuator assembly. Adaptation of the swing knee trajectory based on error in the swing knee trajectory due to variation of the initial stance knee angle of the early swing substate provides a first correction operation to correct or adapt a swing knee trajectory error.

The next substate of the walk mode is the late swing substate, which again corresponds to the second portion of the overall swing substate of a gait cycle that principally is characterized by knee extension of the knee joint component. When the knee joint component begins extending, or when the early swing trajectory completes, the KAFO enters the late swing substate. The late swing substate proceeds similarly to the early swing substate. The KAFO should enter the late swing substate upon completion of the early swing trajectory, but because the late swing substate can also be initiated by knee extension, the peak knee angle at the end of early may not have been reached which can lead to a trajectory error during the late swing substate. To ensure smooth trajectory guidance, the electronic control system modifies the swing knee trajectory during the late swing substate in real time as needed to guide the knee joint component from a variable position at the initiation of the late swing substate to the user's desired stance knee position to return to the stance substate.

Figure 10:
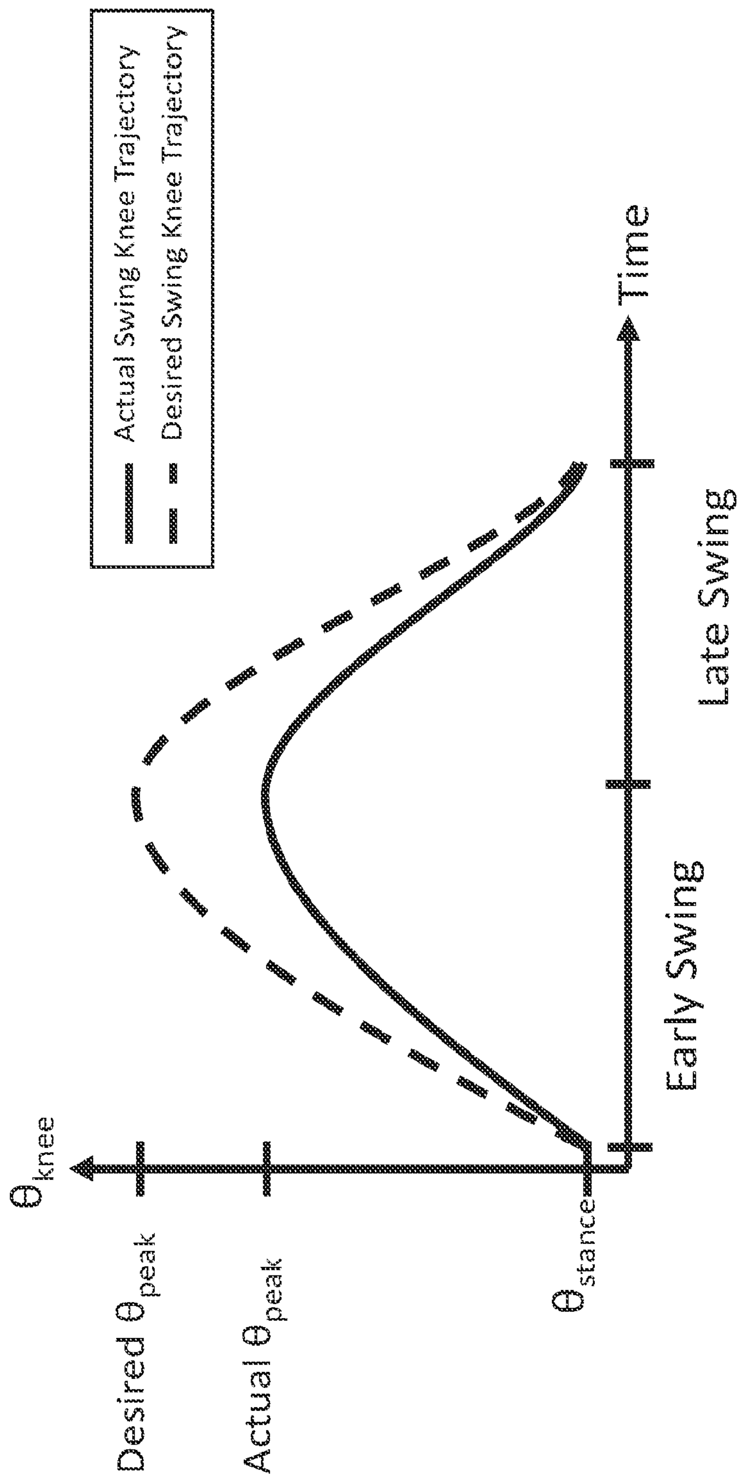
FIG. 10 is a drawing depicting a basis for swing knee trajectory adaptation during a late swing substate.

FIG. 10 is a drawing illustrating a basis for swing knee trajectory adaptation based on an error correction during the late swing substate. As referenced above, for the desired swing knee trajectory (dotted line in FIG. 10), the transition from the early swing substate to the late swing substate occurs when the desired peak knee angle $\theta_{peak}$ is reached, and the knee joint component transitions from knee flexion to knee extension. Due to the nature of impairments associated with users of KAFO devices, as shown FIG. 10 (solid line) the actual swing knee trajectory may correspond to the knee joint component failing to reach the desired peak knee angle $\theta_{peak}$. In other words, the actual peak knee angle that is reached is less than the desired peak knee angle. The result is that the knee joint component begins to extend while the desired swing knee trajectory is associated with continued knee flexion toward the desired peak knee angle. Under such circumstances, the electronic control system trying to further flex the knee joint component toward the desired peak knee angle opposes the user's efforts to extend the knee joint component from the actual peak knee angle that is reached. Such opposing control of the electronic control system would exert resistance against the user's actual gait, which can lead to stumbling and fall.

Figure 11:
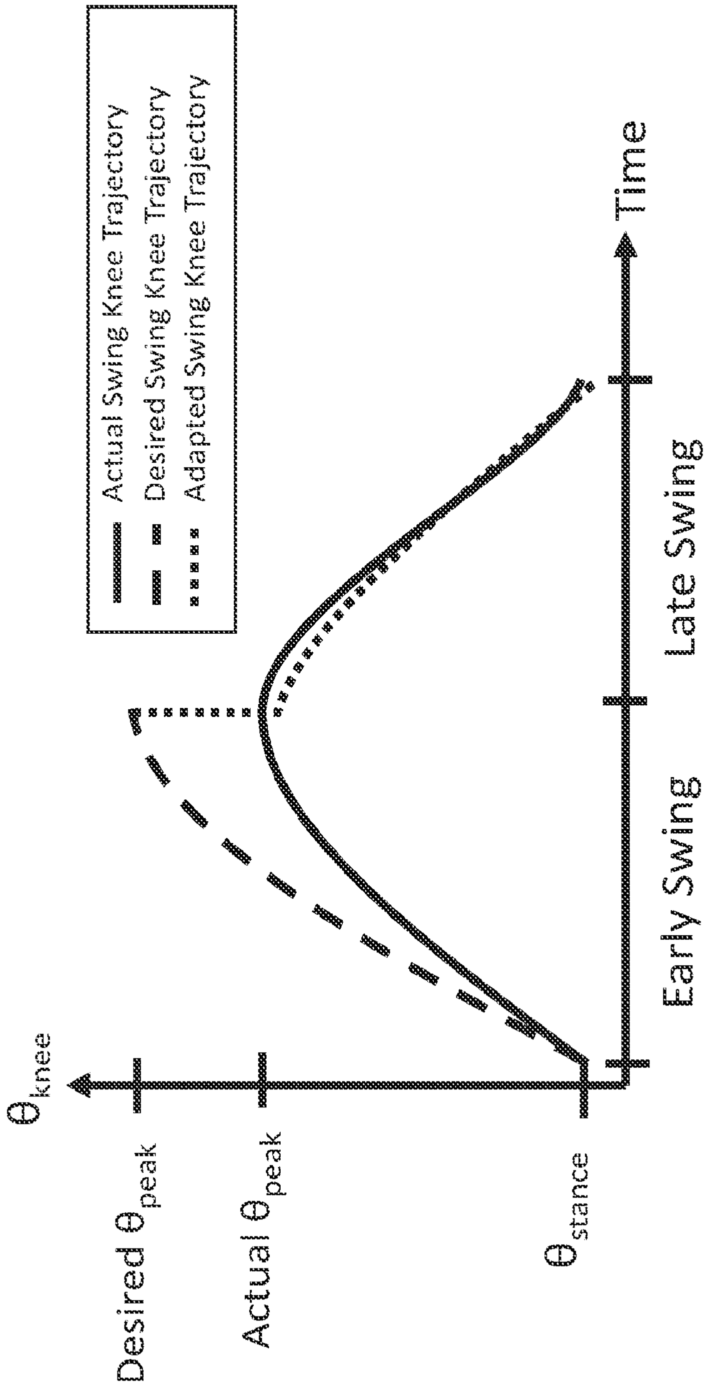
FIG. 11 is a drawing depicting an exemplary trajectory adaptation based on a second error correction during the late swing substate.

Accordingly, the electronic control system performs an error correction operation by which the control system detects that the late swing substate is to be entered prior to the knee joint component flexing to the desired peak knee angle $\theta_{peak}$. FIG. 11 is a drawing depicting an exemplary trajectory adaptation during the late swing substate. Generally, the electronic control system reads the desired knee swing trajectory stored in the system, including reading the desired peak knee angle, and detects the actual swing knee trajectory including the actual peak knee angle. The electronic control system then measures a second swing error between the desired swing knee trajectory and the actual swing knee trajectory at the end of the early swing substate and the initiation of the late swing substate. The second error can be based on the actual peak knee angle of the knee joint component at the end of the early swing substate and initiation of the late swing substate which results in the error relative to the desired peak knee angle $\theta_{peak}$.

FIG. 11 illustrates that when it is detected that the peak knee angle is not being reached and extension is beginning to occur, the late swing trajectory is adapted to proceed from the detected, actual peak angle back to the desired stance angle $\theta_{stance}$. The detection of a failure to reach the desired peak knee angle may be based on one of two conditions. First, if the allotted time associated with the early swing substate of the desired swing knee trajectory is exhausted but the knee angle has not yet reached the desired peak knee angle, then the electronic control system will adapt the late swing knee trajectory. Second, if a knee extension force is detected indicating that the knee joint component is beginning to extend but the knee angle has not yet reached the desired peak knee angle, then the electronic control system also will adapt the late swing knee trajectory. Under either of such conditions, the actual peak knee angle is detected and an error relative to the desired peak knee angle is measured, and the late swing trajectory is modified to control the knee joint component to extend from the measured peak knee angle to the desired stance knee angle, at which point the late swing substate (and the overall swing substate) is complete and the next stance substate begins. Such adaptation is performed for each step.

Referring back to FIG. 7 in combination with FIG. 11, the electronic control system measures a second error (the first error is that of FIG. 9) between the desired swing knee trajectory and the actual swing knee trajectory at the initiation of the late swing substate, and in particular the second error is an error in the actual peak knee angle relative to the desired peak knee angle. When the swing peak knee angle error indicates a failure to reach the desired peak knee angle, the actuator assembly of the powered mobility assistance device is operated to control the knee joint component to adjust the swing knee trajectory during the late swing substate of the gait cycle to extend the knee joint component from the measured peak knee angle to the desired stance knee angle. This second error of the swing knee trajectory also is corrected according to feedback control via the operation of the powered control element ($T_P$) to provide mobility assistance with the actuator assembly. Correction based on error in the swing knee trajectory due to the peak knee angle error at the end of the early swing substate and initiation of the late swing substate provides a second correction operation to correct the swing knee trajectory error.

At the completion of the late swing substate, i.e., upon completion of the swing substate trajectory of the gait cycle, the KAFO returns to the stance substate thereby completing a full gait cycle. The walk mode constitutes the electronic control system implementing multiple gait cycles as described above to perform walking. Through the walk mode substates, swing and stance knee joint component angles may be varied or adjusted as warranted for a given user. Lower limb impairment is often accompanied by a deviation from typical joint kinematics, such as for example a limited range of joint motion. The electronic control system is programmable and operable to adjust the trajectory guidance and control for each user. For example, a desired stance knee angle is adjustable to anywhere from 0° to 20° of flexion, permitting users to walk with a significant amount of flexion during the stance substate as warranted in view of the user's impairment. The desired swing knee trajectory may include a peak knee flexion angle achieved during the swing substate that is also adjustable, for example allowing the user to achieve a peak knee flexion angle from 30° to 100° of knee flexion. This permits the system to provide an adequate amount of foot clearance to a wide range of users with different types and degrees of impairment.

The electronic control system also may perform walking cadence control corresponding to the duration of the swing substate of each step, as indicated generally in FIG. 7. In one example, the swing substate (including the combined early and late swing substates) has a fixed duration based on user capabilities. For example, the fixed swing substate operation permits a user to select a fixed swing phase duration from 0.2 to 2 seconds. The fixed swing substate duration may be programmed by the orthotist into the electronic control system. Each time the user initiates a step, the electronic control system controls the knee joint component to complete the swing substate in this preset amount of time.

In another example, time spent in the stance substate is used to determine cadence in implementing the duration of the early and late swing substates. For example, a fixed duration of the swing substate (which again includes the combined early and late swing substates) may be set and programmed based on a specified ratio of the duration of the swing substate to a duration of the stance substate for a given user based on user capabilities. The specified ratio may be fixed based on representative stance phase duration measurements.

In another example, cadence control may be fully adaptive whereby duration of the swing substate adjusts in real time as the user walks. In this cadence control, a duration of the swing substate is set based on a specified and programmed ratio of the duration of the swing substate to a duration of the stance substate, and the duration of the swing substate adapts in real time based on a duration measurement of one or more previous stance substates. As the stance duration changes with continued walking, the swing substate duration adjusts in accordance with the ratio. Such adaptive cadence control may be performed independently of the trajectory control described above. Adaptive swing speed scales the amount of time it takes to complete the swing trajectory based on the duration of the stance substate of the previous several steps. This results in the swing speed increasing as the user walks more rapidly, thereby spending less time in the stance substate of each step as the user's gait improves. A challenge with adaptive swing duration control is that individual users have varying ratios of stance to swing time, depending upon the gait pattern. For example, one user walking at a cadence of 60 steps per minute may spend 500 ms in stance and 500 ms in swing, while another user also walking at the same cadence of 60 steps per minute may spend 700 ms in stance and only 300 ms in swing. The expected ratio between stance and swing can be set and programmed into the electronic control system and tuned for an individual user so that the user is comfortable walking with a variable cadence and having the electronic control system adapt the swing substate duration to the user's performance.

The stance and trajectory control of the walk mode permits additional control operations that aid in the safety and effectiveness of the KAFO device. An example of such a control operation is active stumble recovery. Because the electronic control system implements trajectory guidance and correction to control the swing phase of the gait cycle, foot scuffing or object collision can be responded to with active assistance via the powered control element controlling the actuator assembly to adjust torque levels, rather than by entering high-resistance states as conventional variable-damping systems do. In the event of foot scuffing or object collision, the electronic control system implements active torque from the actuator assembly to attempt to complete a step, ending with the brake engaged and the knee joint component in an extended position corresponding to standing, thereby implementing recovery from a stumble. In the event that step completion is not possible and a fall potential thereby increases, the electronic control system locks the knee joint component in the stance state to provide the user the ability to weight the limb to aid in recovery to prevent falling when possible.

Another example of such a control operation is to implement predictable fall behavior. The electronic control system is capable of detecting falls and responding to them in a predictable manner. The electronic control system accomplishes this control by first detecting the orientation of the KAFO while in the walk mode based on signals received from the accelerometer and IMU sensors. Should the KAFO device tilt or rotate out of an upright position by an angle greater than an amount indicative of falling, for example greater than 45 degrees, the electronic control system disables mode transitions which would initiate stepping or cause the knee joint component to release stance knee support. The rotation or tilt can be determined based on the angle of the thigh relative to the knee for a frontward or backward fall, or to the left or right relative to the ground for a sideways fall. This control ensures that the knee joint component maintains the performance when the falling tilt or rotation occurred. Transiently passing outside of the range of rotation only prevents transitions until the upright position is reattained. This means that a user performing a conventional adaptive stepping motion, such as for example a marching gait pattern or a high-kick step, will only temporarily and briefly be prohibited from state transitions. However, should the KAFO device maintain a deviation from the upright orientation for a sufficient period of time that indicates actual falling has occurred (e.g., five seconds is suitable), the electronic control system operates to lock the knee joint component. The purpose of such locking is to prevent the KAFO to undergo stepping after a fall has occurred, as the user would be on the ground. Accordingly, when the electronic control system determines that a fall has occurred, the electronic control system places the KAFO device in the lock mode described above to prevent any additional mode transitions until the user manually unlocks the device via the user interface.

Another example of such a control operation is to provide mobility assistance for transition from sitting to standing. Unlike conventional variable resistance KAFO devices, the electronic control system of the KAFO of the current application is capable of providing powered assistance to the knee joint component when transitioning from a sitting to a standing position. This sit-to-stand transition may be triggered by the user placing the KAFO device in the free mode, and with the knee joint component released in the free mode the user can orient the lower limb appropriately to load the foot sensors. Upon the detection of such loading, the electronic control system can operate the knee joint component to initiate standing by providing powered assistance with the actuator assembly to extend the knee.

As another example of such a control operation, different ways to implement mode transitions may be provided. As referenced above, the KAFO includes a user interface with physical buttons which enable deliberate mode transitions between the described walk, lock, and free modes. For advanced users, the KAFO device also can have a double-tap feature enabled or disabled by the user's orthotist to implement mode transitions, which is simpler to perform during use than manipulating the user interface buttons. The double-tap feature when present and enabled permits the user to make transitions between lock mode and walk mode by tapping on the KAFO two times with their fingers within a preset rate, which is detected by the KAFO sensors. For example, the KAFO accelerometer can detect this double-tap signal along the accelerometer axis and provide a double-tap sensor signal to the electronic control system. The electronic control system determines whether the measured taps are within a range of acceleration magnitude and within a certain time range of one another to constitute a mode transition command, whereas the electronic control system ignores other taps or impacts that are not commensurate with a mode transition command to avoid undesired transitions when the double-tap feature is enabled. The double-tap feature in particular may be employed to transition from lock mode to walk mode and vice versa.

As another example of such a control operation, the electronic control system may be configured to implement automatic foot sensor threshold adjustments. The electronic control system may be configured to provide the ability to adjust the sensitivity to pressure of the heel and toe pressure sensors. Some users may have, for example, higher baseline pressure levels due to a tighter fitting brace or lower pressure levels due to very low body mass. Foot sensor threshold pressure levels may be set by the user's orthotist as part of the KAFO device configuration. The electronic control system further may be configured to evaluate and automatically adjust foot sensor threshold pressure levels in response to changes seen in the user's pressure levels based on different circumstances. For example, a tight-fitting pair of shoes might elevate the baseline levels of the pressure readings. Elevated pressure levels could lead to difficulty with step initiation or inappropriate timing of step initiation. To avoid this situation, the electronic control system could automatically adjust the foot sensor threshold pressure levels based on the observed maximum and minimum foot sensor readings during each walking session. For example, the electronic control system may automatically update the thresholds based on the maximum and minimum foot sensor values recorded in the previous 100 steps taken.

As another example of such a control operation, the electronic control system may be configured to implement stairs and slope detection and control. The KAFO device generally is capable of ascending and descending ramps and slopes which meet ADA regulations for accessibility without modification to the KAFO's operation. Users optionally can also negotiate stairs by placing the device in the lock mode and using a step-to-gait pattern as the user would with a locked brace passive KAFO. The electronic control system also may be configured to automatically adjust the operation of the knee joint component in response to detection of a slope or stair ascent or descent based on the accelerometer and/or IMU sensor signals. The electronic control system can modify the knee flexion trajectory to better suit the steepness of the slope being navigated. Likewise, the electronic control system can provide powered knee extension assistance with the actuator assembly driving the knee joint component during stair ascent, and controlled resistance with the actuator assembly can be applied to the knee joint component during stair descent to permit a proper trajectory pattern in either ascent or descent. For typical KAFO users, stair ascent and descent are accomplished by having both feet land on the same step prior to proceeding to the next step. For users with higher mobility capabilities, same-step landing may not be warranted, and the electronic control system instead may implement stair control using a step-over-step ascent and/or descent instead of dual foot landing on same step before proceeding to the next step.

As another example of such a control operation, the electronic control system may be configured to implement enhanced instability detection. As referenced above, a typical foot sensor configuration includes three pressure sensors under the heel and balls of the foot. Because of the discrete nature of these sensors, data can be collected on the progression of the user's center of pressure as the KAFO moves from the heel at heel-strike to the balls of the foot prior to toe-off. The electronic control system can determine the progression of the center of pressure based on the foot sensor measurements, and significant deviations from an anticipated progression pattern (e.g., the center of pressure advancing to a significantly more lateral position on the balls of the foot) could be used as an indicator that the user is becoming unstable. The electronic control system may respond by controlling the knee joint component to prevent release of stance knee support during a detected period of instability.

As another example of such a control operation, the electronic control system may be configured to implement powered assistance via the knee joint component during the early swing substate, followed by late swing adaptation during the late swing substate. In other words, early swing adaptation, such as described above with respect to FIG. 9, would not be performed and early swing control would be implemented simply as powered assistance. Then, should the user not reach the desired peak angle after the early swing substate, actual peak angle detection and late swing adaptation would proceed as descried above in connection with FIGS. 10 and 11. Such swing control may be particularly suitable for user's with greater mobility capabilities, as early swing adaptation may not be warranted for higher capability users.

As another example of such a control operation, the electronic control system may be configured to implement a "silent mode" that does not employ the brake. Of the various components of the actuator assembly, the brake tends to be the most noisy, and thus to enhance user comfort with the device for users with higher mobility capabilities, the brake may be used only when necessary to provide stance support. Instead, stance support may be implement using powered assistance by the motor of the actuator assembly, rather than by braking. As such stance support solely by powered assistance would require more user effort to achieve stable stance support, again, this mode is suitable for users with higher mobility capabilities. Another mode for users of higher mobility capabilities that would not employ the brake may be termed a "jogging mode" for faster and more continuous stepping. In such mode, the brake also would not be used during the stance substate for stance support. This allows a greater amount of knee flexion during the stance substate, which for rapid stepping becomes a shortened substate, to provide more dynamic motion during transitions from step to step when faster stepping is desired.

As another example of such a control operation, the electronic control system may be configured to implement turning or cornering control. As compared to ordinary straight-line stepping, turning or cornering may generate different signals from the sensors. For example, turning or cornering may generate different pressure signals from the lateral versus the medial toe sensors, and/or also may generate a different angular velocity signal from the gyroscope sensor in the IMU. Upon detecting sensor signals associated with turning or cornering, the electronic control system may control operation of the knee joint component to adjust such gait parameters as gait speed, stride length, joint rotation angle, and the like to account for turning or cornering.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of operating a powered mobility assistance device comprising the steps of:

performing a gait cycle including stance control of a knee joint component of the powered mobility assistance device during a stance substate of the gait cycle, and swing control of the knee joint component during a swing substate of the gait cycle, wherein multiple gait cycles of the stance control and the swing control are implemented for walking using the powered mobility assistance device;

wherein the stance control comprises:

reading a desired stance knee angle of the knee joint component that is preset into a control system of the powered mobility assistance device;

detecting an actual stance knee angle of the knee joint component as measured by sensors in the powered mobility assistance device; and measuring an error between the desired stance knee angle and the actual stance knee angle, and when the error between the desired stance knee angle and the actual stance knee angle exceeds a threshold error, operating an actuator assembly of the powered mobility assistance device to control the knee joint component to stabilize the knee joint component during the stance substate of the gait cycle; and wherein the swing control comprises:

reading a desired swing knee trajectory of the knee joint component that is preset into the control system of the powered mobility assistance device, wherein a swing knee trajectory is defined as a pattern of knee flexion and extension of the knee joint component through the swing substate of the gait cycle;

detecting an actual swing knee trajectory of the knee joint component as measured by the sensors in the powered mobility assistance device; and measuring an error between the desired swing knee trajectory and the actual swing knee trajectory, and operating the actuator assembly of the powered mobility assistance device to control the knee joint component to adjust the actual swing knee trajectory toward the desired swing knee trajectory during the swing substate of the gait cycle;

wherein operating the actuator assembly in the stance control comprises combining operation of a resistive control element that resists knee joint component rotation and a powered control element that powers knee joint component rotation to provide an output torque to stabilize the knee joint component during the stance substate; and wherein operating the resistive control element comprises operating a brake in the actuator assembly to resist rotation of the knee joint component, and operating the powered control element comprises operating an actuator in the actuator assembly to provide additional resistance to rotation of the knee joint component to stabilize the knee joint component during the stance control.

2. The method of operating of claim 1, wherein the desired stance knee angle is a knee angle from 0° to 20° of knee flexion.

3. The method of operating of claim 1, wherein the threshold error is 0.1 degrees to two degrees.

4. The method of operating of claim 1, wherein operating the actuator assembly in the swing control comprises operating a powered control element that assists rotation of the knee joint component to provide an output torque to rotate the knee joint component to adjust the swing knee trajectory toward the desired swing knee trajectory during the swing substate.

5. The method of operating of claim 1, wherein the swing substate of the gait cycle includes an early swing substate characterized by knee flexion of the knee joint component, and a first error is measured between a desired knee angle of the knee joint component of the desired swing knee trajectory and an actual knee angle of the knee joint component of the actual swing knee trajectory at the initiation of the early swing substate; and the actuator assembly of the powered mobility assistance device is operated to control the knee joint component to adjust toward the desired swing knee trajectory during the early swing substate of the gait cycle by implementing the desired swing knee trajectory from the actual knee angle.

6. The method of operating of claim 5, wherein the swing substate of the gait cycle further includes a late swing substate following the early swing substate and characterized by knee extension of the knee joint component, and a second error is measured between a desired peak knee angle of the knee joint component of the desired swing knee trajectory and an actual peak knee angle of the knee joint component of the actual swing knee trajectory at the initiation of the late swing substate; and the actuator assembly of the powered mobility assistance device is operated to control the knee joint component to adjust the swing knee trajectory toward the desired swing knee trajectory during the late swing substate of the gait cycle by implementing the swing knee trajectory from the actual peak knee angle toward a desired stance knee angle at the end of the late swing substate.

7. The method of operating of claim 6, wherein the desired swing knee trajectory includes a peak knee angle from 30° to 100° of knee flexion.

8. The method of operating of claim 1, wherein the swing substate has a fixed duration, and the fixed duration is set based on a specified ratio of the duration of the swing substate to a duration of the stance substate based on representative stance substate duration measurements.

9. The method of operating of claim 8, wherein the fixed duration is from 0.2 to 2 seconds.

10. The method of operating of claim 1, wherein a duration of the swing substate is set based on a specified ratio of the duration of the swing substate to a duration of the stance substate, and the duration of the swing substate adapts in real time based on a duration measurement of one or more previous stance substates.

11. The method of operating of claim 1, further comprising a neutral substate that is a transition from the stance substate to the swing substate, wherein during the neutral substate the resistive control element and the powered control element are inactive.

12. The method of operating of claim 11, wherein the sensors include pressure sensors positioned in a foot plate of the mobility assistance device, and the neutral substate is initiated upon detecting the pressure sensors transitioning from being loaded toward being unloaded; and wherein the neutral substate is entered when it is detected from the pressure sensors that a center of pressure of a user's foot has advanced from a heel to a ball of the user's foot.

13. The method of operating of claim 11, wherein the sensors include pressure sensors positioned in a foot plate of the mobility assistance device, and the neutral substate is initiated upon detecting the pressure sensors transitioning from being loaded toward being unloaded; and wherein the neutral substate is entered when it is detected from the pressure sensors that the pressure sensors are fully unloaded.

14. The method of operating of claim 1, wherein the mobility assistance device further is operable in a free mode in which the knee joint component is in an unlocked state and the actuator assembly is maintained inactive; and wherein the mobility assistance device further is operable in a lock mode in which the actuator assembly operates to maintain the knee joint component in a locked state that substantially resists rotation of the knee joint component.

* * * * *